(12) United States Patent
Tsuji et al.

(10) Patent No.: US 7,722,590 B2
(45) Date of Patent: May 25, 2010

(54) PULL-ON DISPOSABLE WEARING ARTICLE

(75) Inventors: Tomoko Tsuji, Kanonji (JP); Hirotomo Mukai, Kanonji (JP); Akiyoshi Kinoshita, Kanonji (JP); Tatsuya Hashimoto, Kanonji (JP)

(73) Assignee: Uni-Charm Corporation, Ehime-Ken (JP)

( * ) Notice: Subject to any disclaimer, the term of this patent is extended or adjusted under 35 U.S.C. 154(b) by 747 days.

(21) Appl. No.: 11/419,113

(22) Filed: May 18, 2006

(65) Prior Publication Data

US 2006/0264859 A1 Nov. 23, 2006

(30) Foreign Application Priority Data

May 19, 2005 (JP) .............................. 2005-146338
Apr. 20, 2006 (JP) .............................. 2006-117166

(51) Int. Cl.
*A61F 13/15* (2006.01)
*A61F 13/20* (2006.01)

(52) U.S. Cl. ............................ 604/385.28; 604/385.01; 604/385.27

(58) Field of Classification Search ................. 604/358, 604/367, 370, 378–380, 385.01, 385.21, 604/385.04, 385.24–385.28

See application file for complete search history.

(56) References Cited

U.S. PATENT DOCUMENTS

| 5,476,458 A | 12/1995 | Glaug et al. |
| 2005/0288645 A1 * | 12/2005 | LaVon ................... 604/385.21 |

FOREIGN PATENT DOCUMENTS

| EP | 0 873 738 A2 | 10/1998 |
| EP | 1 080 708 A2 | 3/2001 |
| JP | 06-054878 B2 | 3/1994 |
| JP | 2004-041311 B2 | 2/2004 |

* cited by examiner

*Primary Examiner*—Michele Kidwell
(74) *Attorney, Agent, or Firm*—Morrison & Foerster LLP

(57) ABSTRACT

A pull-on disposable wearing article is provided with a chassis and an absorbent batt structure extending on the inner surface of the chassis. The chassis has a front waist region, a rear waist region and a crotch region and is composed of a base sheet which is substantially not elastically extensible/contractible, and first and second outer sheets stretched in a transverse direction and bonded in such a stretched state to outer surfaces of the base sheet in the front and rear waist regions, respectively, and being elastically extendible/contractible in the transverse direction. An absorbent batt structure is laid inside the chassis. The base sheet defining an inner surface of the chassis is formed with gathers as the first and second outer sheets contract.

10 Claims, 6 Drawing Sheets

PULL-ON DISPOSABLE WEARING ARTICLE

This application claims priority of Japanese Patent Application Nos. 2005-146338, filed May 19, 2005, and 2006-117166, filed Apr. 20, 2006, which are herein incorporated by reference in their entirety.

BACKGROUND OF THE INVENTION

The present invention relates generally to a pull-on disposable wearing article and particularly to such wearing articles suitable for a pull-on incontinence diaper, a pull-on disposable diaper for infants, a disposable training pant for babies, and particularly for a pull-on disposable incontinence diaper.

The conventional pull-on disposable wearing article has often been focused to meet the demand for good fitness of the article when the article is put on the wearer's body and consequentially a front waist region as well as a rear waist region has been constructed to be elastically extensible/contractible overall in a circumferential direction. For example, Japanese Patent Publication No. 3581373 (hereinafter referred to as "REFERENCE 1") discloses a pull-on disposable diaper wherein the front and rear waist regions include elastic members sandwiched between inner and outer sheets thereof.

Japanese Unexamined Patent Application Publication Nos. 1987-231005, 1987-243806 and 1987-243807 (hereinafter referred to as "REFERENCE 2", "REFERENCE 3" and "REFERENCE 4", respectively) disclose disposable absorbent pants having an absorbent core and a crotch region provided along bottoms of respective concavely curving side edges with relatively wide elastic members.

Japanese Patent Publication No. 3616077 (hereinafter referred to as "REFERENCE 5") discloses a disposable diaper having an absorbent layer provided with at least three grooves extending from a crotch region into front and rear waist regions.

According to the disclosure of REFERENCE 1, the inner and outer sheets of the front and rear waist regions are formed with gathers as the elastic members contract. The gathers formed on the outer surfaces of the front and rear waist regions are not only undesirable for appearance of the diaper but also apt to catch on something, causing a state of the article put on the wearer's body to be disordered or material of the waist regions to be damaged.

According to the disclosure of REFERENCES 2-4, any specific technical significance of the relatively wide elastic members attached to the crotch region along the bottoms of the concavely curving side edges is not referred to. Particularly, no technical significance of the correlation between the relatively wide elastic members and the absorbing effect can be found in the disclosure. In view of this, use of such relatively wide elastic members is not considered to be based on any technical significance.

According to the disclosure of REFERENCE 5, a central region of a flat absorbent layer is deformed along the grooves to present a W-shaped cross-section while transversely opposite side edges are bent downward as the diaper is put on the wearer's body. The side edges bent downward in this manner come in close contact with the inner sides of the wearer's thighs. In general, the absorbent layer has a stiffness higher than those of the remaining components of the diaper, and the side edges of such stiff absorbent layer being bent downward and coming in close contact with the inner sides of the wearer's thighs inevitably causes the wearer to experience somewhat discomfort feeling. Furthermore, the W-shaped cross-section appearing when this absorbent layer is deformed presents many folds, i.e., crests and troughs since the side edges also are folded downward. Therefore, it is not ensured that the absorbent layer is reliably folded or deformed in the predetermined shape.

SUMMARY OF THE INVENTION

In view of the problems as have been described above, it is an object of the present invention to solve the problems of the conventional pull-on disposable wearing articles.

According to the present invention, there is provided a pull-on disposable wearing article comprising a chassis having a longitudinal axis and a transverse axis being orthogonal to each other and an absorbent batt structure. The chassis comprises a front waist region made of a thermoplastic fibrous nonwoven fabric including a front waist band member adapted to be elastically extensible in a direction defined by the transverse axis but substantially not elastically extensible in a direction defined by the longitudinal axis, a rear waist region made of thermoplastic fibrous nonwoven fabric including a rear waist band member adapted to be elastically extensible in a direction defined by the transverse axis but substantially not elastically extensible in a direction defined by the longitudinal axis and a crotch region being substantially not elastically extensible at least in the direction defined by the longitudinal axis, side edges of the crotch region opposite to each other in the direction defined by the transverse axis describing curves concaved by a predetermined depth toward the longitudinal axis as viewed with the chassis as a whole developed with the front and rear waist regions unfolded away from each other, a waist-hole, a pair of legholes, and the batt structure extending on an inner surface of the chassis between the front and rear waist regions.

The article according to the present invention further comprises a base sheet, first and second outer sheets and a pair of liquid-resistant crotch side sheets. The base sheet has the front and rear waist regions, the crotch region and the concavely curved side edges thereof and is substantially not elastically extensible at least in the direction defined by the longitudinal axis. The first and second outer sheets are elastically extensible in the direction defined by the transverse direction and bonded to respective outer surfaces of the front and rear waist regions of the base sheet while the first and second outer sheets are stretched in the direction defined by said transverse axis so that the base sheet is formed with gathers as the first and second outer sheets contract. The crotch side sheets, each having a proximal edge, a free edge and opposite ends and being elastically extensible in the direction defined by the longitudinal axis, have the proximal edges bonded to the crotch region along vicinities of bottoms of the concavely curving edges below the side edges of the batt structure and the opposite ends bonded to the front and rear waist regions so that, when the article is put on the wearer's body, non-bonded zones of the crotch side sheets including the free edges are freely extensible/contractible with respect to the side edges of the batt structure and extend outward approximately from side edges of a liquid-absorbent zone of the batt structure corresponding to the side edges of the crotch region.

The present invention may include preferred embodiments as follow:

The liquid-absorbent zone is defined by a liquid-absorbent core, and the core is provided in vicinities of the side edges with a pair of first fold-guide channels spaced from each other in the direction defined by the transverse axis and extending in the direction defined by the longitudinal axis.

The core is provided between the pair of first fold-guide channels with a second fold-guide channel extending from the crotch region into the front and rear waist regions.

The core is provided in vicinities of the first fold-guide channels with a pair of ears extending outward in the direction defined by the transverse axis.

The article further comprises a pair of liquid-resistant barrier flaps each having a proximal edge, a free edge and opposite ends, the proximal edges being fixed between the respective side edges of the batt structure and the paired crotch side sheets, the barrier flaps being adapted to rise above the crotch side sheets as said barrier flaps contract.

A dimension by which the non-bonded zone including the free edge of the crotch side sheet extends outward in the direction defined by the transverse axis is preferably in a range of 10 to 50 mm as measured at the bottom of the concave curve.

Each of the leg-holes presents, as viewed from the front of the front waist region, a substantially triangular shape defined by a lower end of the front waist region linearly extending in the direction defined by the transverse axis, one of the side edges of the crotch region obliquely curving toward the longitudinal axis and one of lower side edges of the rear waist region extending obliquely and linearly between the side edge and the lower end, and through this substantially triangular leg-hole the base sheet formed with the gathers is partially exposed.

The chassis is treated in regions of the first and second outer sheets respectively defining the front and rear waist regions overlying the core so that these regions of the first and second outer sheets substantially lose initial elastic extensibility in the direction defined by the transverse axis.

The article further comprises a liquid-resistant barrier sheet having a size at least corresponding to the liquid-absorbent zone of the batt structure and underlying the liquid-absorbent zone.

The chassis further includes a third outer sheet having no elastic extensibility, and the third outer sheet extends between the front and rear waist regions so as to cover the outer surface of the crotch region.

The first and second outer sheets and the base sheet are bonded together by a plurality of bonding lines extending intermittently or continuously in the direction defined by the longitudinal axis.

In the case of a pull-on disposable wearing article according to the present invention, the front and rear waist regions comprise the base sheet which is substantially not extensible/contractible at least in the direction defined by the longitudinal axis and the first and second outer sheets which are respectively bonded to the front and rear waist regions of the base sheet and elastically extensible/contractible in the direction defined by the transverse axis. Consequentially, the front and rear waist regions of the base sheet lying inside are formed with gathers providing air-permeability between the wearer's skin and the article as the first and second outer sheets contract. However, the first and second outer sheets defining the outer surfaces of the front and rear waist regions are not formed with any gathers except waist band members. In this way, there is neither apprehension that appearance of the article might be deteriorated nor possibility that the article might catch on something, causing a state of the article put on the wearer's body to be disordered or material of the waist regions to be damaged.

The front and rear waist regions are not elastically extensible in the direction defined by the longitudinal axis, and such a feature allows the crotch side sheets to be elastically extensible toward the inner sides of the wearer's thighs and to be bent downward as the article is put on the wearer's body. Consequentially, the article can be smoothly lifted up so as to come in close contact with the wearer's skin. With the article put on the wearer's body in this manner, the base sheet lying inside the front and rear waist regions is formed with gathers, but the outer surfaces of the front and waist regions are not formed with irregular gathers since the first and second outer sheets of the front and rear waist regions are elastically extensible sheets. The crotch region also is not formed with irregular gathers and comes in surface-contact with the inner sides of the wearer's thighs since the crotch side sheets also are elastically extensible sheets. With the article put on the wearer's body, the free edges of the respective crotch side sheets are collapsed downward due to friction with the inner sides of the wearer's thighs and contribute to reliable prevention of body fluids from the wearer's crotch.

The article according to the present invention allows the wearer to visually recognize the leg-holes through the waist-hole broadened by the wearer to put the article on the body and to insert the legs through the respective leg-holes without a problem that the wearer's toes might catch on the peripheral edges of the leg-holes. With the article put on the wearer's body, the elastic contractile force of the crotch side sheets causes the ears of the core to rise above the barrier flaps along the first fold-guide channels so as to define the side walls. Being compressed between the inner sides of the wearer's thighs, the core is deformed along the second fold-guide channel so as to present a W-shaped cross-section. The crotch side sheets function to keep this W-shaped cross-section. Therefore, so far as the article is properly put on the wearer's body, the crests of the W-shaped cross-section are maintained in substantial contact with the outer surface of the wearer's excretory organ to prevent body fluids from movement onto the wearer's skin. In addition, the crotch side sheets promote body fluids to flow into the troughs of the W-shaped cross-section and alleviate the possibility that body fluids might come into contact with the wearer's skin.

DETAILED DESCRIPTION OF THE PREFERRED EMBODIMENTS

Details of a pull-on disposable wearing article according to the present invention will be more fully understood from the description of a pull-on disposable diaper as a preferred embodiment thereof as given hereunder with reference to the accompanying drawings.

Figure 1:
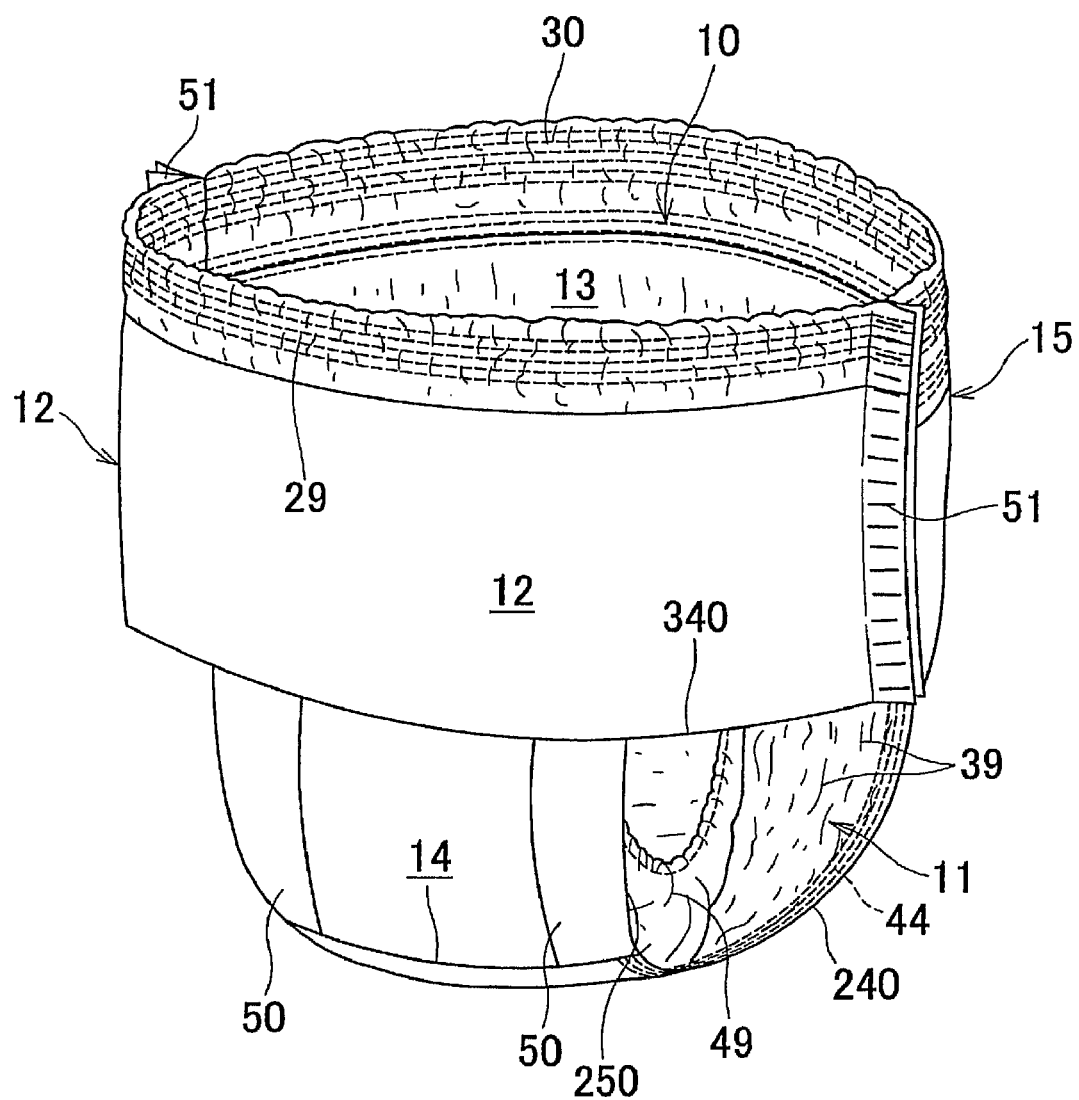
FIG. 1 is a perspective view showing a pull-on disposable diaper as an embodiment of a pull-on disposable wearing article according to the present invention.
Figure 2:
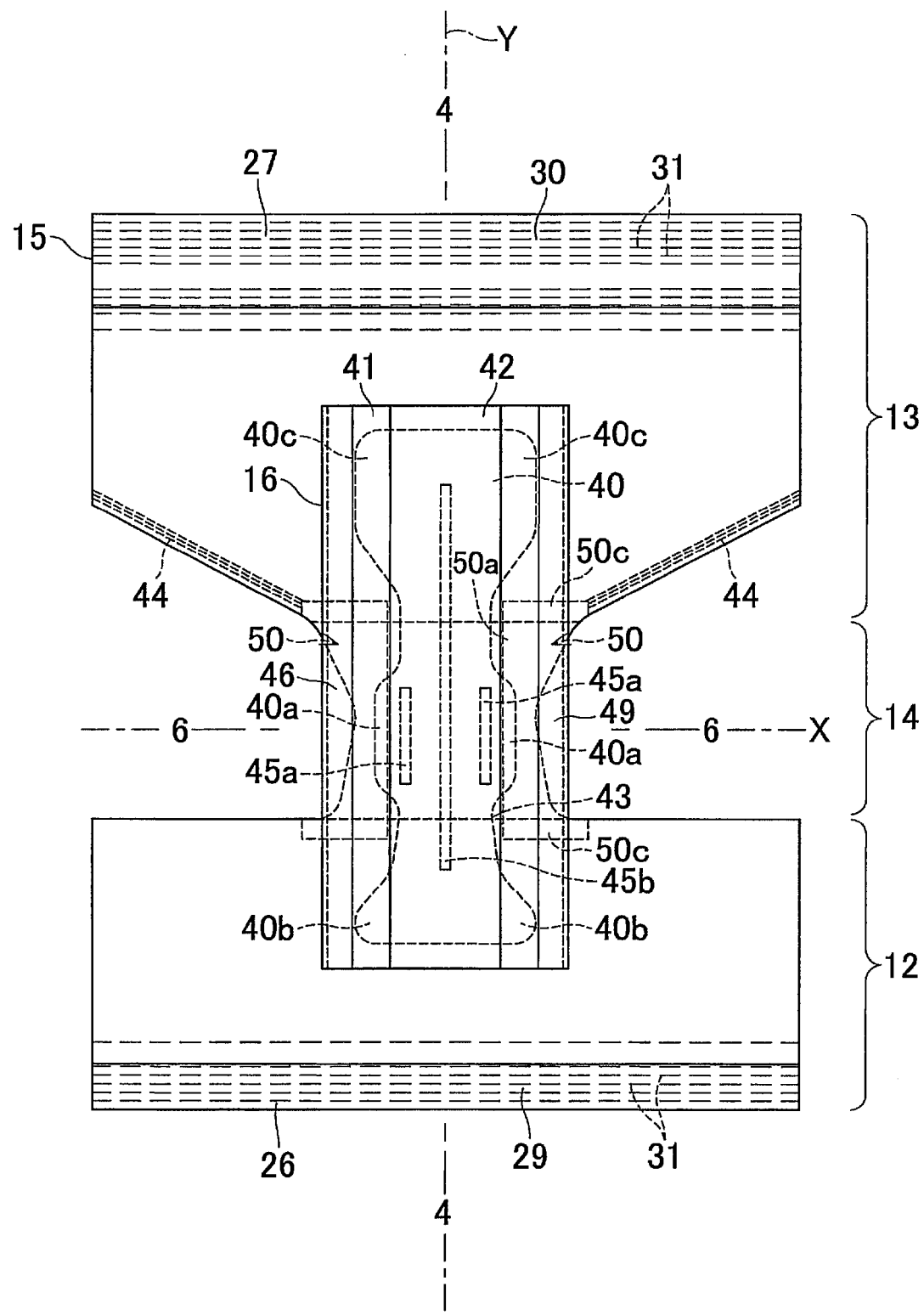
FIG. 2 is an unfolded plan view showing the diaper with front and rear waist regions unfolded away from each other.

Referring to FIGS. 1 and 2, a diaper is of the pull-on type having front and rear waist regions previously connected with each other and comprises a longitudinal axis Y, a transverse axis X, a waist-hole 10, a pair of leg-holes 11, the front waist region 12, the rear waist region 13 and a crotch region 14. It will be appreciated that the longitudinal and transverse axes Y, X respectively correspond to the lines in FIG. 2 along which respective sectional views are taken. The diaper comprises a chassis 15 and an absorbent batt structure 16. The batt structure 16 extends on an inner side of the chassis 15 between the front and rear waist regions 12, 13 in the direction defined by the longitudinal axis Y. It should be noted here that the batt structure 16 is slightly put aside toward a front end of the chassis 15 from the viewpoint of relative position with the chassis 15.

Referring now to FIGS. 2 through 5, the chassis 15 comprises a base sheet 19 which is not elastically extensible in the longitudinal and transverse axes Y, X (as seen in FIG. 2) or at least in the longitudinal direction Y and an outer sheet 37. The outer sheet 37 comprises, in turn, a first outer sheet 20 and a second outer sheet 21 both of which are elastically extensible in the direction defined by the transverse axis X but substantially inextensible in the direction defined by the longitudinal direction Y, and a third outer sheet 22 which is inextensible in both directions defined by the longitudinal and transverse axes Y, X, respectively. The base sheet 19 is composed of a front waist region 112, a crotch region 114 and a rear waist region 113 being contiguous one to another in this order. On the assumption of an imaginary straight line along which the front waist region 112 is contiguous to the crotch region 114, the front waist region 112 will present a rectangular shape which is relatively long in the direction defined by the transverse axis X. On the assumption of an imaginary straight line along which the rear waist region 113 is contiguous to the crotch region 114, the rear waist region 113 will present a trapezoidal shape. The rear waist region 113 having such shape has an area which is sufficiently larger than an area of the front waist region 112 to cover the wearer's back. The crotch region 114 has opposite side edges slightly curving inward.

Figure 3:
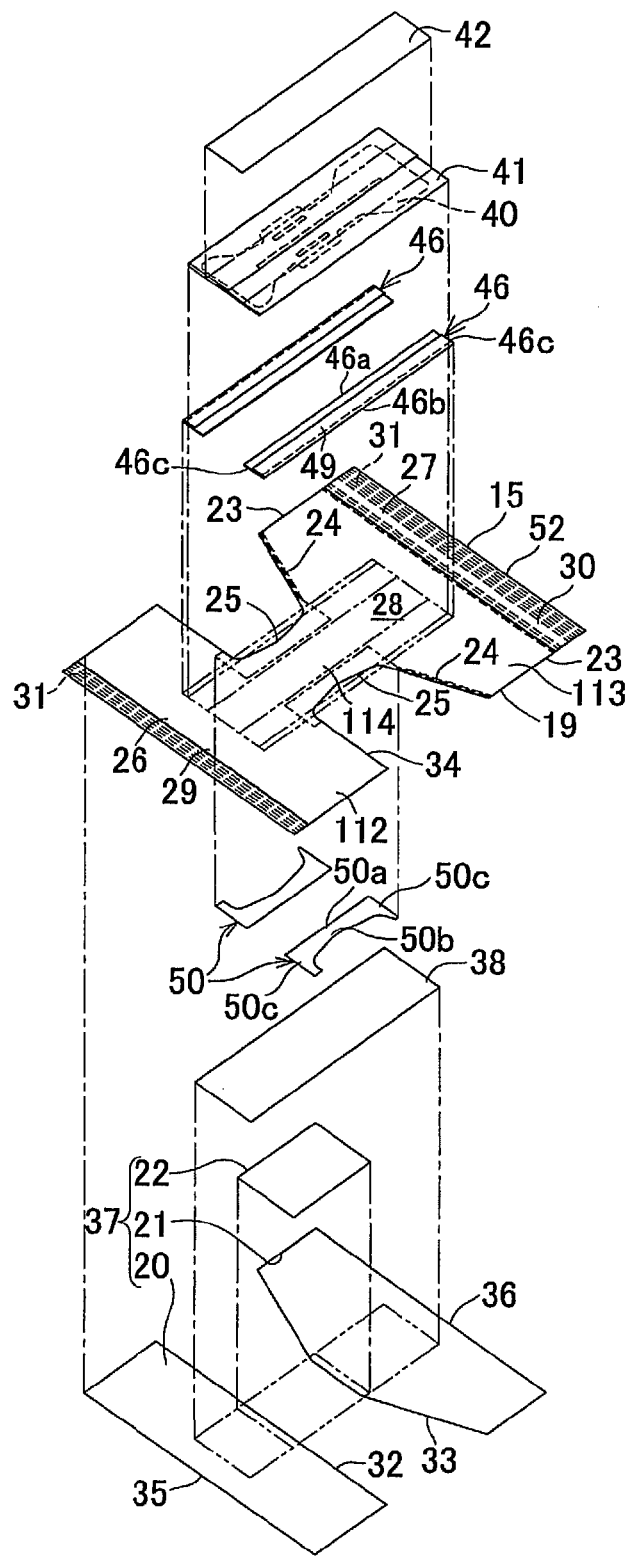
FIG. 3 is an exploded perspective view of the diaper.

As will be apparent from FIG. 3, the first outer sheet 20 and the second outer sheet 21 have substantially the same shapes as those of the front waist region 112 and the rear waist region 113 of the base sheet 19, respectively, except that the first and second outer sheet 20, 21 are smaller than the front and rear waist regions 112, 113, respectively, so far as the dimension as measured in the direction defined by the longitudinal axis Y is concerned. The third outer sheet 22 is connected between the first and second outer sheets 20, 21 by a suitable means such as hot melt adhesive or welding technique (not shown) and destined to be placed on an outer surface of the crotch region 114 of the base sheet 19. In this manner, the first and second outer sheets 20, 21 are connected with each other with interposition of the third outer sheet 22. Alternatively, the first, second and third outer sheets 20, 21, 22 may be integrated together in the form of a fibrous nonwoven fabric sheet which is the same as the first and second outer sheets instead of providing the third outer sheet 22 separately of the first and second outer sheets 20, 21. In this case, a zone corresponding to the third outer sheet may be, for example, heat-treated so that the extensibility of this zone is lost.

Figure 4:
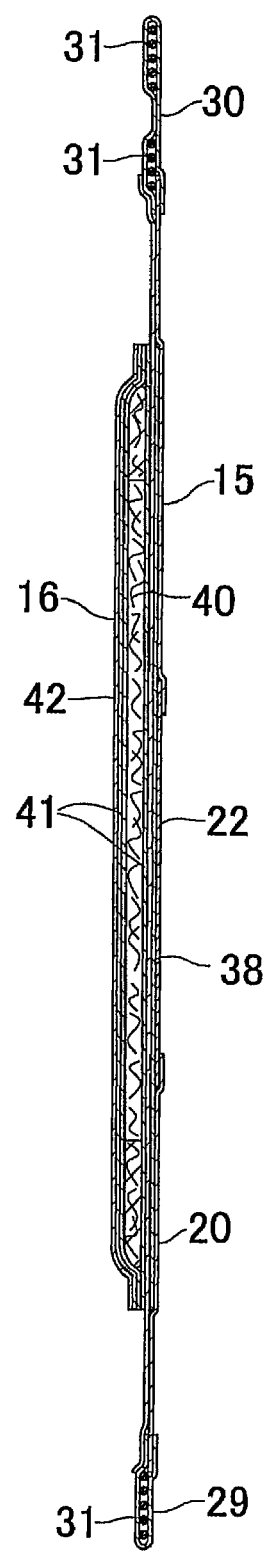
FIG. 4 is a scale-enlarged sectional view taken along the line 4-4 in FIG. 2.

As shown in FIGS. 3 and 4 (See FIG. 1 also), the front and rear waist regions 12, 13 are provided along respective ends thereof with front and rear waist band members 29, 30, respectively. Each of these front and rear waist band members 29, 30 comprises a thermoplastic synthetic fibrous nonwoven fabric which is not elastically extensible in the direction defined by the longitudinal axis Y and a plurality of elastic members 31 which are elastically extensible in the direction defined by the transverse axis X. Specifically, these elastic members 31 are interposed between respective halves of the nonwoven fabric folded in two. In this case, the nonwoven fabric is folded in two so as to sandwich the respective ends of the chassis 15 and then bonded to the respective ends of the chassis 15 in the front and rear waist regions 12, 13, respectively, by hot melt adhesive (not shown). Typically, the rear waist band member 30 has a dimension as measured in the direction defined by the longitudinal axis Y larger than a corresponding dimension of the front waist band member 29, and the number of the elastic members 31 for the rear waist band member 30 is more than the number of the elastic members 31 for the front waist band member 29. Alternatively, the front and rear waist band members 29, 30 may be formed by folding back the respective ends of chassis 15 in the front and rear waist regions 12, 13 instead of using the nonwoven fabric provided separately of the chassis 15. The elastic members 31 used for the front and rear waist band members 29, 30 preferably exhibit a stress up to 10N/50 mm as they are stretched by 50 to 150%.

While the base sheet 19 may be an appropriate thermoplastic synthetic fibrous nonwoven fabric which is not elastically extensible in the directions defined by the longitudinal and transverse axes Y, X or at least in the direction defined by the longitudinal axis Y, for example, a polyolefin-based spun bond nonwoven fabric having a basis weight in a range of 10 to 50 g/m$^2$ is suitable for use as the base sheet 19. The first and second outer sheets 20, 21 are preferably formed from a spun bond nonwoven fabric made of polyurethane resin/polypropylene resin fiber blend which was blended at a ratio of 65:35 to 25:75 so as to have a basis weight in a range of 20 to 50 g/m$^2$ and then subjected to drawing treatment through a pair of geared rolls.

The first and second outer sheets 20, 21 are bonded, with these sheets 20, 21 being stretched by 50 to 150%, for example, in the direction defined by the transverse axis X (corresponding to the machine direction for a raw fabric in the course of manufacturing), to the respective outer surfaces of the front and rear waist regions 112, 113 of the base sheet 19 by hot melt adhesives (not shown) so that the front and rear waist regions 12, 13 may elastically come in close contact with the wearer's skin. The base sheet 19 which is not elastically extensible is formed with gathers 39 (See FIG. 1) as the first and second outer sheets 20, 21 contract in the direction defined by the transverse axis X. Orientation as well as pattern of these gathers 39 depends on a pattern in which hot melt adhesives are coated. More specifically, hot melt adhesives are coated intermittently or continuously in the direction defined by the longitudinal axis Y in various patterns such as stripe, spiral and zigzag patterns. For example, if hot melt adhesives are intermittently or continuously coated in the direction defined by the longitudinal axis Y so as to extend linearly, a plurality of gathers 39 each extending substantially in the direction defined by the longitudinal axis Y will be formed along said pattern. When hot melt adhesives are coated intermittently in the direction defined by the longitudinal axis Y, these lines of hot melt adhesives preferably extend in a zigzag alignment.

These gathers 39 define channels which cooperate with high air-permeability provided by the base sheet 19 itself to assure further higher air-permeability between the base sheet 19 and the wearer's skin. These gathers 39 can be seen through the leg-holes in FIG. 1. More specifically, as will be apparent from FIG. 1 showing the diaper from the front of the front waist region 12, a lower end 340 of the front waist region 12 linearly extending in the direction defined by the transverse axis X, one of side edges 250 of the crotch region 14 obliquely curving toward the longitudinal axis Y and one of lower side edges 240 of the rear waist region 13 extending obliquely and linearly between said side edge 250 and the lower end 340 (See FIG. 2) define a substantially triangular leg-hole through which the base sheet 19 formed with the gathers 39 is partially seen. The leg-holes 11 each having such a shape are sufficiently visible through the waist-hole 10 broadened when the diaper is put on the wearer's body. The gathers 39 would deteriorate the appearance of the article if they are formed on the outer surface of the article. In the case of the diaper according to the invention, the gathers 39 are formed only on the inner surface of the article and consequentially the respective inner surfaces of the front and rear waist regions 12, 13 provide comfortable touch and high air-permeability. Conveniently, consumers of the article are not required to broaden the waist-hole 10 and to peer through the interior of the article before the effect of the gathers can be confirmed. Obviously, the gathers 39 are concealed by the wearer's legs inserted through the leg-holes 11 after the article has been put on the wearer's body. It will be apparent that none of the gathers is formed in the crotch region 14 of the not elastically extensible chassis 15 since the first and second outer sheets 20, 21 are not present in this crotch region 14.

To avoid a possibility that the front and rear waist regions 12, 13 might become bulky, it is preferred that the gathers 39 are kept to be uniformly collapsed toward a predetermined side as viewed in the direction defined by the transverse axis X, for example, leftward or rightward in FIG. 1.

As shown in FIGS. 1 and 2, along the lower side edges 240 of the rear waist region 13 partially defining the leg-holes 11 are optionally provided thread-like elastic members 44. These elastic members 44 may be tape-like members instead of thread-like members.

In a region of the chassis 15 corresponding to a liquid-absorbent region of the batt structure 16, the first and second outer sheets 20, 21 are appropriately treated, for example, heat treated while these sheets 20, 21 are appropriately extended in the direction defined by the transverse axis X so that these sheets 20, 21 may lose initial elastic extensibility. In such a state, the batt structure is bonded at least except opposite lateral zones thereof to the treated zone of the chassis 15 and the base sheet 19 in the crotch region 14. In this way, there is no anxiety that the batt structure 16 might be undesirably deformed due to contraction of the first and second outer sheets 20, 21 and the batt structure 16 might create a feeling of discomfort against the wearer and/or absorbency might be deteriorated. Instead of the heat treatment, loss of elastic extensibility may be achieved also by coating the region of the base sheet 19 to be bonded to the batt structure with hot melt adhesives or by bonding a suitable sheet such as a thermoplastic synthetic fibrous nonwoven fabric which is not elastically extensible in the directions defined by the longitudinal and transverse axes Y, X to the region of the base sheet 19.

As shown in FIG. 1, the front and rear waist regions 12, 13 of the chassis 15 are detachably bonded together along respective opposite side edges 51, for example, by welding intermittently in the direction defined by the longitudinal axis Y so as to obtain the pull-on type diaper.

Figure 5:
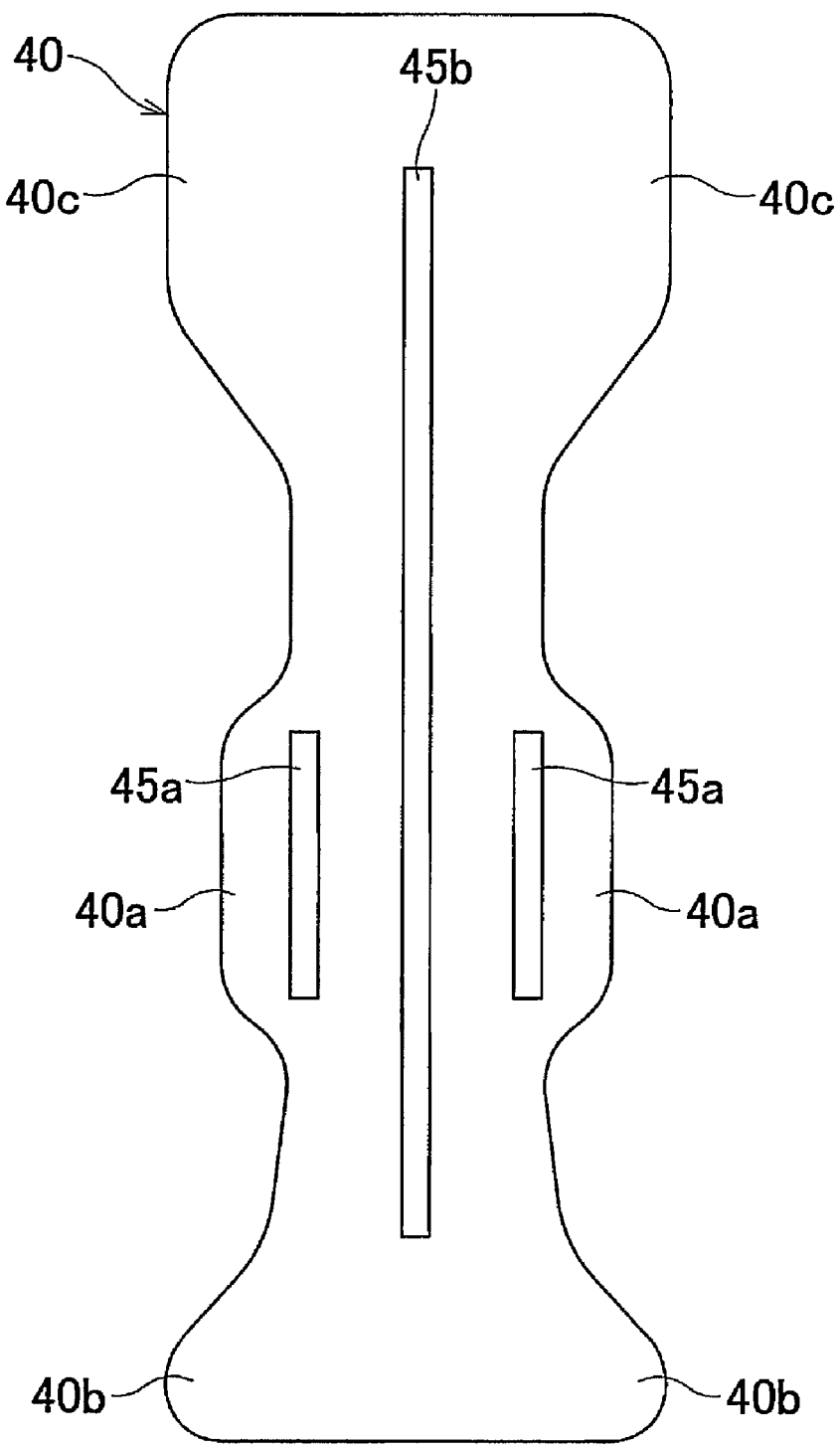
FIG. 5 is a scale-enlarged plan view of an absorbent core.

As will be apparent from FIGS. 2 and 5 (See FIGS. 6 through 8 also), the batt structure 16 comprises the liquid-absorbent core 40 formed from a mixture of fluff pulp as principal material and super-absorbent polymer particles or the like, a liquid-pervious wrap sheet 41 underlying the core 40 and folded back upward to wrap the core 40, and a topsheet 42 centrally bonded to an upper surface of the wrap sheet 41. With the batt structure 16 fixed to the chassis 15 at a predetermined position (See FIG. 2), the core 40 is provided with respective pairs of ears 40a, 40b, 40c extending outward from side edges thereof in opposite end zones and a substantially middle zone of the crotch region 14 (See FIG. 5). The core 40 is provided immediately inside the ears 40a with a pair of fold-guide channels 45a extending in the direction defined by the longitudinal axis Y and between these fold-guide channels 45a with a single fold-guide channel 45b extending also in the direction defined by the longitudinal axis Y into the front and rear waist regions 12, 13, more specifically, extending at least to a point overlying the wearer's buttock cleft when the article is put on the wearer's body. These channels may be replaced by compressed grooves or lower material density zones.

The batt structure 16 is provided at lower side edges thereof with liquid-resistant barrier flaps 46 extending outward in the direction defined by the transverse axis X. Each of the barrier flaps 46 has a proximal edge 46a, a free edge 46b and opposite ends 46c and comprises a liquid-resistant fibrous sheet 49 folded in two, elastic member 47 wrapped by the free edge 46b folded back and extending in the direction defined by the longitudinal axis Y, and a plastic film strip 48 underlying the elastic member 47 and being elastically extensible in the direction defined by the longitudinal axis Y. The barrier flaps 46 are fixed along the respective proximal edges 46a to the lower side edges of the batt structure 16 and fixed at the opposite ends 46c to the upper surface of the batt structure 16. The barrier flaps 46 are adapted to rise above crotch side sheets 50 which will be described later as the elastic members 47 and the film strips 48 contract (See FIGS. 1, 6 and 7). The barrier flaps 46 preferably have a tensile stress lower than that of the front and rear waist band members 29, 30.

Figure 6:
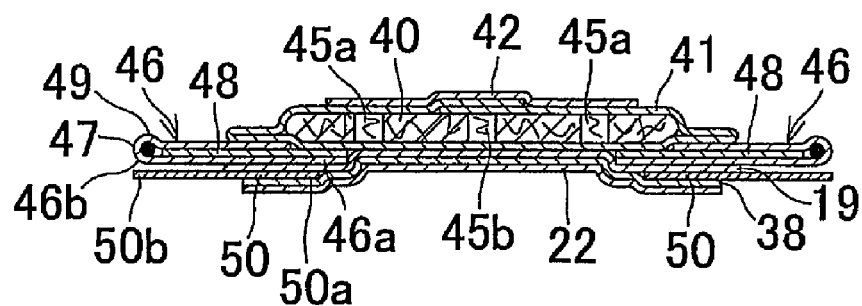
FIG. 6 is a scale-enlarged sectional view taken along the line 6-6 in FIG. 2.
Figure 7:
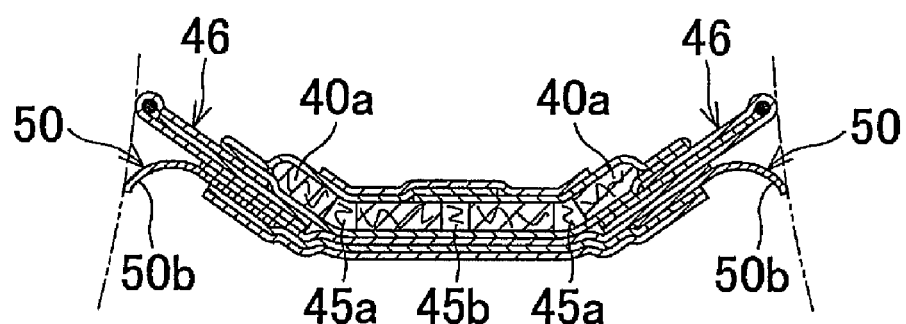
FIG. 7 is a sectional view of the absorbent batt structure as this structure has been deformed from a state shown in FIG. 6 along a pair of channels extending in longitudinal direction in the vicinity of opposite side edges of the structure.
Figure 8:
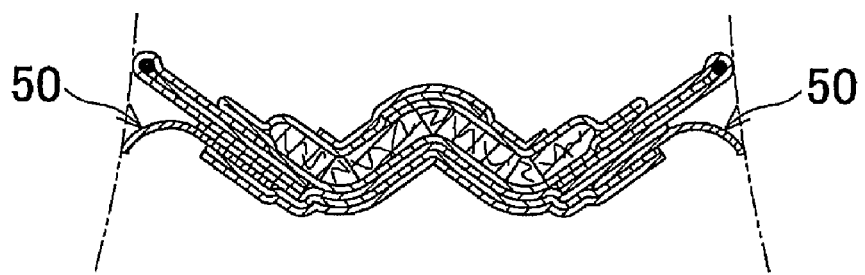
FIG. 8 is a sectional view of the batt structure as this structure has been further deformed from a state shown in FIG. 7 along an intermediate channel interposed between said pair of lateral channels and extending also in the longitudinal direction.

Referring to FIGS. 6 through 8 (See FIGS. 1 through 3 also), the crotch region 14 of the base sheet 19 is provided along opposite side edges thereof with a pair of crotch side sheets 50 which are elastically extensible at least in the direction defined by the longitudinal axis Y and extend outward in the direction defined by the transverse axis X. More specifically, each of these crotch side sheets 50 has a proximal edge 50a, a free edge 50b and opposite ends 50c. Below the respective barrier flaps 46, the crotch side sheets 50 are stretched at least in the direction defined by the longitudinal axis Y and bonded in such a stretched state along the proximal edges 50a to the concavely curving edges of the crotch region 14 in the vicinity of the bottom thereof while the opposite ends 50c are also bonded to the chassis 15 in the front and rear waist regions 12, 13. Consequentially, the non-bonded zones of the respective crotch side sheets 50 including the respective free edges 50b are freely extensible with respect to the side edges of the batt structure 16 so that these non-bonded zones may extend outward in the direction defined by the transverse axis X from the vicinity of the side edges of the liquid-absorbent region in the batt structure 16 when the article is put on the wearer's body. The crotch side sheets 50 having the non-bonded zones extending outward in this manner are vertically spaced from the rising barrier flaps 46 and at least the free edges 50b extend outward in the direction defined by the transverse axis X from the outer edges of the barrier flaps 46. A dimension by which the crotch side sheet 50 except the proximal edge 50a, i.e., the non-bonded zone including the free edge 50b extends outward in the direction defined by the transverse axis X is preferably in a range of 10 to 50 mm as measured at the bottom of the concave curve. Such specific dimensioning cooperates with the tensile stress of the crotch side sheet 50 to cause the ear 40a of the core 40 to rise up so as to define a side wall and thereby to put the crotch side sheet 50 in stably close contact with the inner side of the wearer's thigh. While the crotch side sheet 50 preferably has the same material quality and the tensile stress as those of the chassis 15, it is also possible to use an elastically extensible film or a laminate composed of such film and fibrous nonwoven fabric as a stock material for the crotch side sheet 50.

While the crotch side sheet 50 have been described above with respect to the case in which the crotch side sheets 50 are formed as the member separate of the chassis 15, the crotch region 14 interposed between the elastically extensible first and second outer sheets 20, 21 defining the front and rear waist regions 12, 13 may be formed from the same material as those of the outer sheets 20, 21 and contiguous to these outer sheets 20, 21. In this case, the crotch region 14 is heat treated for loss of extensibility except the side edges thereof so that these side edges may function as the crotch side sheets 50.

As will be understood from the description given below in reference with FIG. 2, it is preferable for the crotch side sheets 50 to lie immediately outside the ears 40a of the core 40.

The liquid-resistant, preferably liquid-impervious barrier sheet 38 is interposed between the outer sheet 37 and the base sheet 19 so as to lie in the liquid-absorbent zone of the batt structure 16, particularly in the region of the liquid-absorbent core. It should be understood that the barrier sheet 38 may be interposed between the batt structure 16 and the base sheet 19.

Now the function of the crotch region 14 according to the embodiment of the present invention will be discussed here. With the article put on the wearer's body, the crotch side sheets 50 each being relatively wide in the crotch region 14 as seen in FIGS. 7 and 8 are elastically stretched and bent downward so as to come in close contact with the inner sides of the wearer's thighs. With the article put on the wearer's body, the elastic contraction of the crotch side sheets 50 causes the ears 40a of the core 40 to be driven upward from below the barrier flaps 46 along the first fold-guide channels 45a and thereby to define the side walls which functions as liquid-barriers. The core 40 is further deformed along the second fold-guide channel 45b to present a W-shaped cross-section as the core 40 is compressed between the inner sides of the wearer's thighs. A central convex of this W-shaped cross-section lies at least along the wearer's buttock cleft. The elastically contractile force of the crotch side sheets 50 functions to keep the cross-section of the crotch region 14 in the W-shape. Consequently, the crotch region 14 is stabilized in close contact with the inner sides of the wearer's thighs. In this manner, the crotch side sheets 50, the ears 40a of the core 40 and at least the first fold-guide channels 45a have an important correlation to optimize the configuration of the crotch region 14.

What is claimed is:

1. A pull-on disposable wearing article having a waist-hole and a pair of leg-holes comprising;
   an absorbent batt structure;
   a chassis comprising:
      a longitudinal axis and a transverse axis being orthogonal to each other;
      a base sheet having:
         a front waist region made of a thermoplastic fibrous nonwoven fabric including a front waist band member adapted to be elastically extensible in a direction defined by said transverse axis but substantially not elastically extensible in a direction defined by said longitudinal axis,
         a rear waist region made of a thermoplastic fibrous nonwoven fabric including a rear waist band member adapted to be elastically extensible in a direction defined by said transverse axis but substantially not elastically extensible in a direction defined by said longitudinal axis, and
         a crotch region being substantially not elastically extensible at least in the direction defined by said longitudinal axis, side edges of said crotch region opposite to each other in the direction defined by said transverse axis describing curves concaved by a predetermined depth toward the longitudinal axis as viewed with said chassis as a whole developed with said front and rear waist regions unfolded away from each other;
   wherein said batt structure extends on an inner surface of said chassis between said front and rear waist regions,
   wherein the base sheet is substantially not elastically extensible in the direction defined by said longitudinal axis and said transverse axis,
   a first outer sheet and a second outer sheet being elastically extensible in the direction defined by said transverse direction and bonded to respective outer surfaces of said front and rear waist regions of said base sheet by a plurality of bonding lines extending continuously in the direction defined by said longitudinal axis while said first and second outer sheets being stretched in the direction defined by said transverse axis;
   wherein said base sheet is formed with a plurality of gathers along said plurality of said bonding lines in said front and rear waist regions as said first and second outer sheets contract, with said plurality of gathers defining channels which continuously extend in the direction defined by said longitudinal axis and are uniformly collapsed toward a predetermined side as viewed in the direction defined by said transverse axis; and
   a pair of liquid-resistant crotch side sheets, each having a proximal edge, a free edge and opposite ends and being elastically extensible in the direction defined by said longitudinal axis, having said proximal edges bonded to said crotch region along vicinities of bottoms of said concavely curving edges below side edges of said batt structure and said opposite ends bonded to said front and rear waist regions so that, when the article is put on the wearer's body, non-bonded zones of said crotch side sheets including said free edges are freely extensible/contractible with respect to said side edges of said batt structure and extend outward approximately from side edges of a liquid-absorbent zone of said batt structure corresponding to said side edges of said crotch region.

2. The article defined by claim 1, wherein said liquid-absorbent zone is defined by a liquid-absorbent core and said core is provided in vicinities of said side edges with a pair of first fold-guide channels spaced from each other in the direction defined by said transverse axis and extending in the direction defined by said longitudinal axis.

3. The article defined by claim 2, wherein said core is provided between said pair of first fold-guide channels with a second fold-guide channel extending from said crotch region into said front and rear waist regions.

4. The article defined by claim 2, wherein said core is provided in vicinities of said first fold-guide channels with a pair of ears extending outward in the direction defined by said transverse axis.

5. The article defined by claim 1, further comprising a pair of liquid-resistant barrier flaps each having a proximal edge, a free edge and opposite ends, said proximal edges being fixed between the respective side edges of said batt structure and said paired crotch side sheets, said barrier flaps being adapted to rise above said crotch side sheets as said barrier flaps contract.

6. The article defined by claim 1, wherein a dimension by which said non-bonded zone including said free edge of said crotch side sheet extends outward in the direction defined by the transverse axis is in a range of 10 to 50 mm as measured at the bottom of a concaved curve.

7. The article defined by claim 1, wherein each of said leg-holes presents, as viewed from the front of said front waist region, a substantially triangular shape defined by a lower end of said front waist region linearly extending in the direction defined by said transverse axis, one of said side edges of said crotch region obliquely curving toward said longitudinal axis and one of lower side edges of said rear waist region extending obliquely and linearly between said side edge and said lower end, and through this substantially triangular leg-hole said base sheet formed with said gathers is partially exposed.

8. The article defined by claim 1, wherein said chassis is treated in regions of said first and second outer sheets respectively defining said front and rear waist regions overlying said core so that these regions of said first and second outer sheets substantially lose initial elastic extensibility in the direction defined by said transverse axis.

9. The article defined by claim 1, further comprising a liquid-resistant barrier sheet having a size at least corresponding to at least said liquid-absorbent zone of said batt structure and underlying said liquid-absorbent zone.

10. The article defined by claim 1, wherein said chassis further includes a third outer sheet having no elastic extensibility and said third outer sheet extends between said front and rear waist regions so as to cover the outer surface of said crotch region.

* * * * *